(12) United States Patent
Creagan et al.

(10) Patent No.: US 6,783,837 B1
(45) Date of Patent: Aug. 31, 2004

(54) FIBROUS CREASED FABRICS

(75) Inventors: Christopher Cosgrove Creagan, Marietta, GA (US); Samuel Edward Marmon, Melbourne, FL (US)

(73) Assignee: Kimberly-Clark Worldwide, Inc., Neehan, WI (US)

( * ) Notice: Subject to any disclaimer, the term of this patent is extended or adjusted under 35 U.S.C. 154(b) by 0 days.

(21) Appl. No.: 09/410,999

(22) Filed: Oct. 1, 1999

(51) Int. Cl.[7] .............................................. A61F 13/15
(52) U.S. Cl. ....................... 428/152; 428/219; 428/913; 442/327; 442/334; 442/352; 442/353; 442/381; 442/382; 604/365; 604/366; 604/378; 604/381; 604/384
(58) Field of Search ................................ 428/152, 131, 428/219, 913; 442/327, 334, 352, 353, 354, 361, 381, 382, 394, 398, 409; 604/365, 366, 378, 381, 384

(56) References Cited

U.S. PATENT DOCUMENTS

| | | | |
|---|---|---|---|
| 75,036 A | 3/1868 | Manheim | 128/2 |
| 810,126 A | 1/1906 | Green | 128/290 |
| 3,855,046 A | 12/1974 | Hansen et al. | 161/150 |
| 3,875,942 A * | 4/1975 | Roberts et al. | 604/370 |
| 4,111,733 A | 9/1978 | Periers | 156/204 |
| 4,340,563 A | 7/1982 | Appel et al. | 264/518 |
| 4,389,211 A | 6/1983 | Lenaghan | 604/383 |
| RE31,599 E | 6/1984 | Rasen et al. | 156/167 |
| 4,546,027 A | 10/1985 | Holvoet et al. | 428/109 |
| 4,559,050 A | 12/1985 | Iskra | 604/368 |
| 4,568,341 A | 2/1986 | Mitchell et al. | 604/368 |
| 4,576,853 A | 3/1986 | Vaughn et al. | 428/181 |
| 4,605,402 A | 8/1986 | Iskra | 604/368 |
| 4,685,914 A | 8/1987 | Holtman | 604/368 |
| 5,057,368 A | 10/1991 | Largman et al. | 428/397 |
| 5,069,970 A | 12/1991 | Largman et al. | 428/373 |
| 5,167,740 A | 12/1992 | Michaelis et al. | 156/73.1 |
| 5,192,606 A * | 3/1993 | Proxmire et al. | 428/284 |
| 5,277,976 A | 1/1994 | Hogle et al. | 428/397 |
| 5,368,926 A * | 11/1994 | Thompson et al. | 428/284 |
| 5,382,400 A | 1/1995 | Pike et al. | 264/168 |
| 5,397,632 A | 3/1995 | Murphy, Jr. et al. | 428/284 |
| 5,466,410 A | 11/1995 | Hills | 264/172.11 |
| H1511 H | 12/1995 | Chappell et al. | 604/383 |
| 5,486,166 A * | 1/1996 | Bishop et al. | 604/366 |
| 5,558,924 A | 9/1996 | Chien et al. | 428/181 |

(List continued on next page.)

FOREIGN PATENT DOCUMENTS

| | | | | |
|---|---|---|---|---|
| CZ | 235494 | 11/1986 | | D04H/1/00 |
| CZ | 263075 | 1/1990 | | D04H/1/54 |
| EP | 0 556 749 | 8/1993 | | A61F/13/15 |
| EP | 0 831 162 | 3/1998 | | D04H/13/00 |
| WO | 94/05243 | 3/1994 | | A61F/13/15 |
| WO | 96/26697 | 9/1996 | | A61F/13/15 |
| WO | 97/18783 | 5/1997 | | A61F/13/15 |

OTHER PUBLICATIONS

Oct. 1997 issue of *Nonwovens Industry* magazine, p. 74, article entitled, "What's New in Highloft Production?" by Krema, Jirsak, Hanus and Saunders.

Primary Examiner—Sandra M. Nolan
Assistant Examiner—Alicia Chevalier
(74) Attorney, Agent, or Firm—James B. Robinson; Ralph H. Dean, Jr.

(57) ABSTRACT

There is provided a surge material for personal care products with a first creased layer and at least a second layer, where the layers are in face-to-face relation to one another and bonded together. The first has creases with a depth of between 0.25 and 2 mm and a frequency of between 5 and 100 per centimeter in the cross-machine and the second layer may have densities of between 0.01 and 0.05 g/cc and a basis weight between 25 and 250 gsm.

22 Claims, 1 Drawing Sheet

U.S. PATENT DOCUMENTS

| | | | | |
|---|---|---|---|---|
| 5,597,647 A | * | 1/1997 | Powers | 442/382 |
| 5,620,545 A | | 4/1997 | Braun et al. | 156/205 |
| 5,639,700 A | | 6/1997 | Braun et al. | 442/340 |
| 5,656,368 A | | 8/1997 | Braun et al. | 428/141 |
| 5,681,302 A | | 10/1997 | Melbye et al. | 604/373 |
| 5,695,376 A | * | 12/1997 | Datta et al. | 442/334 |
| 5,753,343 A | | 5/1998 | Braun et al. | 428/141 |
| 5,763,078 A | | 6/1998 | Braun et al. | 428/365 |
| 5,804,295 A | | 9/1998 | Braun et al. | 428/323 |
| 5,814,390 A | | 9/1998 | Stokes et al. | 428/181 |
| 5,820,973 A | | 10/1998 | Dodge, II et al. | 428/212 |
| 5,879,343 A | | 3/1999 | Dodge, II et al. | 604/378 |
| 5,888,607 A | | 3/1999 | Seth et al. | 428/92 |
| 5,906,879 A | | 5/1999 | Huntoon et al. | 428/136 |

* cited by examiner

US 6,783,837 B1

FIBROUS CREASED FABRICS

FIELD OF THE INVENTION

The invention is related to the fields of fluid handling and filtration. Suitable uses include absorbent personal care products. More particularly, it concerns a fabric having creases which results in good resilience and resistance to compression, versus comparable materials having an un-creased structure.

BACKGROUND OF THE INVENTION

Personal care products, as well as filtration products, must have the ability to control the movement of fluid to some degree. Such control is often accomplished by manipulating the pore size, density, fiber denier, bonding area or other physical characteristics of the components of the product. Chemical means for controlling the characteristics are also used and include surfactants, applied both internally and externally.

Personal care products usually have a surge layer interposed between and in intimate, liquid communicating contact with a top sheet and another layer such as a distribution or retention layer. The surge layer is usually adjacent the inner (away from a wearer) surface of the top sheet, which is the outermost surface of the product that contacts the wearer. It is usually desirable to attach the upper and/or lower surfaces of the surge layer to the top sheet and next layer to further enhance liquid transfer.

Previous surge layers have included single and multi-layer structures having varying densities, deniers and the like. Examples of such previous surge materials may be found in U.S. Pat. Nos. 5,879,343 and 5,820,973 to Dodge et al. Though such surge materials have generally been successful, a more resilient or compression resistant surge material is still desired for better fluid handling capability under a load. A surge material that could better control the direction of fluid movement would also be desired.

There remains a need, therefore, for a surge material for personal care products and for filtration that is capable of retaining its integrity during pressure loads while also being able to better control the direction of fluid movement. It is an object of this invention to provide such a novel structure.

SUMMARY OF THE INVENTION

The objects of the invention are achieved by a surge layer for personal care products with a first creased layer and at least a second layer. The layers are in face-to-face relation to one another and bonded together. The first layer should have a basis weight between 5 and 70 gsm and the second layer may have densities of between 0.01 and 0.05 g/cc and a basis weight between 25 and 250 gsm.

DEFINITIONS

Figure 1:
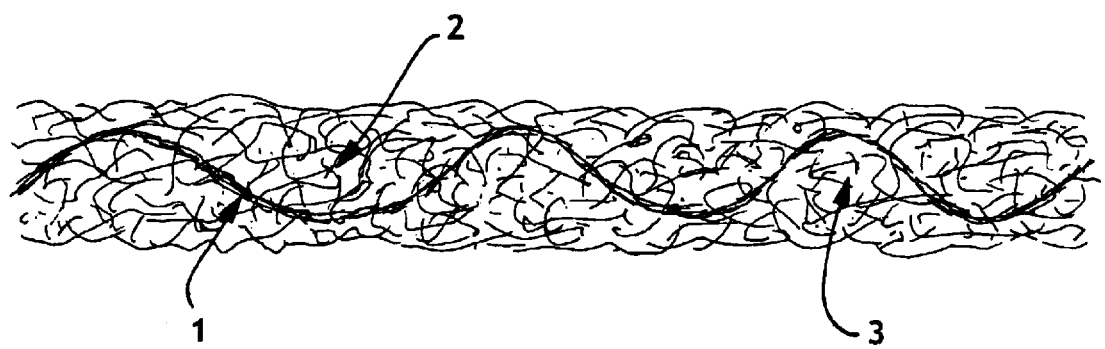
FIG. 1 shows a cross-section of a structure wherein the first, creased layer is surrounded by a low density layer on either side, producing a fabric having a creased core layer within a low density blanket.

"Disposable" includes being disposed of after a single use and not intended to be washed and reused.

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, airlaying processes, and bonded carded web processes. The basis weight of non-woven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers that are formed by extruding molten thermoplastic material as filaments from a plurality of fine capillaries of a spinneret. Such a process is disclosed in, for example, U.S. Pat. No. 4,340,563 to Appel et al. and others. The fibers may also have shapes such as those described in U.S. Pat. Nos. 5,277,976, 5,466,410, 5,069,970 and 5,057,368, which describe fibers with unconventional shapes.

"Conjugate fibers" refers to fibers which have been formed from at least two polymers arranged in substantially constantly positioned distinct zones across the cross-section of the fibers and which extend continuously along the length of the fibers. Conjugate fibers are taught in, for example, in U.S. Pat. No. 5,382,400 to Pike et al.

As used herein, through-air bonding or "TAB" means a process of bonding a nonwoven bicomponent fiber web or other adhesive containing web, wherein air, hot enough to melt one of the polymers of the bicomponent fibers or other adhesive of which the web is made, is forced through the web. The air velocity is usually between 100 and 500 feet per minute and the dwell time may be as long as 6 seconds. The melting and resolidification of the polymer or adhesive provides the bonding. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

One suitable bonding method for nonwoven webs is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. One example of a pattern is the Hansen Pennings or "HP" pattern with about a 30% bond area with about 200 bonds/square inch as taught in U.S. Pat. No. 3,855,046 to Hansen and Pennings. Numerous other bonding patterns exist. Another suitable and well-known bonding method, particularly when using conjugate staple fibers, is through-air bonding, wherein hot air is passed through the web, at least partially melting a component of the web to create bonds.

"Personal care product" means diapers, training pants, absorbent underpants, adult incontinence products, feminine hygiene products and wound care items like bandages.

"Target area" refers to the area or position on a personal care product where an insult is normally delivered by a wearer.

TEST METHODS

Multiple Insult Test (MIST Evaluation)

Figure 2:
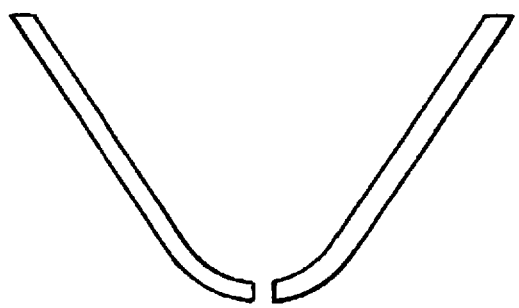
FIG. 2 shows the cross section of a cradle to simulate body curvature of a user such as an infant, which is used in the MIST test.

In this test a fabric, material or structure composed of two or more materials is placed in an acrylic cradle to simulate body curvature of a user such as an infant. Such a cradle is illustrated in FIG. 2. The cradle has a width into the page of the drawing as shown of 33 cm and the ends are blocked off, a height of 19 cm, an inner distance between the upper arms of 30.5 cm and an angle between the upper arms of 60 degrees. The cradle has a 6.5 mm wide slot at the lowest point running the length of the cradle into the page.

The material to be tested is placed on a piece of polyethylene film the same size as the sample and placed in the cradle. The material to be tested is insulted with 80 ml of a saline solution of 8.5 grams of sodium chloride per liter, at a rate of 20 cc/sec with a nozzle normal to the center of the material and ¼ inch (6.4 mm) above the material. The amount of overflow (runoff) is recorded. The difference between the weight of the wet and dry sample and the overflow is the fluid held. The material is immediately removed from the cradle, weighed, and placed on a dry 40/60 pulp/superabsorbent pad having a density of 0.2 g/cc in a horizontal position under 0.01 psi pressure and weighed after 5, 15 and 30 minutes to determine fluid desorption from the material into the superabsorbent pad as well as fluid retention in the material. The pulp fluff and superabsorbent used in this test is Coosa River's CR-2054 pulp and Stockhausen Company's (of Greensboro, N.C. 27406) FAVOR 870 superabsorbent though other comparable pulp and superabsorbents could be used provided they yield a desorption pad of 500 gsm and 0.2 g/cc which after immersion into saline solution under free-swell conditions for 5 minutes, retains at least 20 grams of saline solution per gram of desorption pad after being covered with an air impermeable flexible film and subjected to an air pressure differential of about 0.5 psi (about 3.45 kPa) applied across the thickness of the pad for 5 minutes. This test is repeated using fresh desorption pads on each insult so that a total of three insults are introduced. Five tests of each sample material are recommended.

Material Caliper (Thickness)

The caliper of a material is a measure of thickness and is measured at two different pressures; 0.05 and 0.20 Psi, using a Starret-type bulk tester.

DETAILED DESCRIPTION

A personal care product usually includes a top sheet, which during use is nearest a wearer, a liquid impervious backsheet and an absorbent core of some kind, between the top sheet and backsheet. The top sheet is the first layer in contact with liquid or other exudate from the wearer and so further serves to isolate the wearer's skin from the liquids held in an absorbent structure. The top sheet should be compliant, soft feeling and non-irritating. The backsheet is usually a film that does not allow liquid to pass outwardly from the product. The backsheet protects the clothing and bedding of the user by not permitting exudates to reach them. The absorbent core is usually formed of pulp or a mixture of pulp and superabsorbent and is designed to quickly absorb and retain liquids.

A surge layer is most typically interposed between and in intimate, liquid communicating contact with the top sheet and another layer such as a distribution or absorbent core layer. The surge layer is usually subjacent the inner (unexposed) surface of the top sheet. To further enhance liquid transfer, it can be desirable to attach the upper and/or lower surfaces of the surge layer to the top sheet and next layer, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, the surge layer is adhesively bonded to the top sheet, the amount of adhesive add-on should be sufficient to provide the desired level(s) of bonding, without excessively restricting the flow of liquid from the top sheet into the surge layer.

Various foams and woven and nonwoven webs have been used to construct a surge layer. Surge layers have been, for example, a nonwoven fabric layer composed of a spunbond web of polyolefin filaments. Such nonwoven fabric layers may include conjugate, biconstituent and homopolymer fibers of staple or other lengths and mixtures of such fibers with other types of fibers. Surge layers have also been a bonded carded web or an airlaid web composed of natural and/or synthetic fibers.

Surge layers have been composed of substantially hydrophobic material, and the hydrophobic material has been treated with a surfactant or otherwise processed to impart a desired level of wettability and hydrophilicity. In addition to surfactants, other chemical treatments may be added to the material of the invention. One area of increasing consumer interest is in the area of "skin wellness" treatments like, for example, aloe, which is believed by many to positively affect skin health. Other skin wellness chemicals are known in the art.

The instant invention successfully unites the compression resistance of creased fabrics with the softness and pliability of un-creased nonwoven webs. The resultant web has fluid handling ability superior to that of both a creased layer alone and a nonwoven web alone.

A number of examples of methods of making creased fabrics may be found in, for example, U.S. Pat. Nos. 4,111,733, 5,167,740, 5,558,924 and 5,620,545, each of which is incorporated herein by reference in its entirety. Another method may be found in the October 1997 issue of *Nonwovens Industry* magazine at page 74 in an article by Krema, Jirsak, Hanus and Saunders entitled "What's New in Highloft Production?" as well as in Czech patents 235494 entitled "Fibre Layer, Method of its Production and Equipment for Application of Fibre Layer Production Method" issued May 15, 1995 and 263075 entitled "Method for Voluminous Bonded Textiles Production" issued Apr. 14, 1989. The vibrating lapper and the rotary lapper therein described are commercially available from Georgia Textile Machinery of Dalton, Ga., USA.

Figure 3:
FIG. 3 is a schematic illustration of a cross-section of a creased web according to the teachings of U.S. Pat. No. 5,814,390.

Another method of creasing the fabric useful in this invention may be found in U.S. Pat. No. 5,814,390, commonly assigned, to Stokes et al. Stokes teaches that a nonwoven fabric may be formed, heated and directed through rolls having complementary grooves that deform the web, producing creases. The rolls may be grooved in the machine or cross-machine direction to produce a web that is creased in one or the other direction. Changing the depth and width of the grooves on the rolls results in fabrics having different creases. The fabric may be creased with at least 2 creases per centimeter measured orthogonal to the creases with a bulk after creasing of at least about 1.5 times the thickness of the un-creased web. The web has a stretch recovery of at least 35 percent when stretched 10 percent in a direction orthogonal to the creases. FIG. 3 is a schematic illustration of a cross-section of a creased web according to the teachings of Stokes et al.

One method of making the surge layer of this invention is to produce a first nonwoven web made by, for example, the spunbonding process, and to crease it according to the teachings of Stokes et al. It should be noted that creasing the web increases its density and stiffness. A second nonwoven web may then be produced onto the first layer and the two layers bonded in a through-air bonder. Since the second web is un-creased, its density is less than that of the first layer. This results in a structure having a relatively high density creased first layer and a relatively low density un-creased second layer. A third layer may also be produced onto the two layer structure on the other side of the creased layer, resulting in a three-layer structure. The first creased layer provides compression resistance and the second and third lower density layers provide fiber fill in the valleys of the creases, that is necessary to control fluid movement in the valleys.

Bonding in a through-air bonder is one option for integrating the structure of the invention. In through-air bonding, one component of the structure melts before others and bonds the layers together when it solidifies upon cooling. This process is usually used for conjugate or bicomponent fiber. In the practice of this invention, the first creased layer may be made from bicomponent fibers so that it will bond with fibrous layers on either side of it upon heating. Alternatively, the second and third layers may be made from bicomponent fibers with the same result upon through-air bonding. It is also possible to use bicomponent fibers for all of the layers.

An alternate method of bonding the layers together is through the use of adhesives, powder bonding or other methods known to those skilled in the art.

It is preferred that the creased layer of this invention have creases with a depth of between 0.25 and 2 mm and frequency of between 5 and 100 per centimeter and be in the cross-machine direction. The first layer should have a basis weight between 5 and 70 gsm. The second and third layers may have densities of between 0.01 and 0.05 g/cc and a basis weight between 25 and 250 gsm.

FIG. 1 shows a cross-section of such a structure wherein the first, creased layer 1 is surrounded by a second low density layer 2 and a third low density layer 3. Still more additional layers may be added to this structure to produce a laminate of many layers.

One specific example according to this invention would include a first layer made of 1.2 denier polyethylene/polypropylene conjugate fibers at a basis weight of 27.1 gsm (0.8 osy) and a density of 0.067 g/cc prior to creasing. Such a first layer was made and creased according to U.S. Pat. No. 5,814,390 with creases having a depth of 1.5 mm and frequency of 3.5 per centimeter in the cross-machine direction. Polyethylene/polypropylene conjugate fibers were formed by the spunbond process onto the creased fabric sequentially on both sides and the fabric bonded together by the through-air bonding process between depositions. The second and third layers had densities of between 0.02 and 0.03 g/cc and a basis weight between 67 and 170 gsm (2 and 5 osy). The material had a thickness at 0.05 psi of 273 mils, and at 0.2 psi of 218 mils and a density at 0.05 psi of 0.029 g/cc and at 0.2 psi of 0.036 g/cc. This material was tested according to the MIST Evaluation test.

A control sample of a two layer through-air bonded structure of 6 denier polyester fibers as one layer and 3 denier polyethylene/polypropylene conjugate fibers as the second layer was also made and tested according to the same test. Two controls samples were tested and the results averaged for a basis weight of 177 gsm, a thickness at 0.05 psi of 276 mils, and at 0.2 psi of 191 mils, and a density at 0.05 psi of 0.025 g/cc and at 0.2 psi of 0.037 g/cc.

The average results for three insults and two samples of each material are given in the Table below.

TABLE

|  | Control | Sample |
|---|---|---|
| Overflow, gm | 48.5 | 43.5 |
| Fluid held, gm | 31.7 | 36.7 |
| Total insult, gm | 80.2 | 80.2 |
| Fluid held, gm/gm | 15.9 | 16.2 |
| Percent void volume utilized | 38 | 44 |
| Fluid retained, gm | 1.57 | 0.81 |
| Fluid retained, gm/gm | 0.79 | 0.36 |

It can be seen that the sample material according to the invention had superior results in every category. Thickness retention, overflow, insult volume retained and void volume utilization were all superior to the control.

As will be appreciated by those skilled in the art, changes and variations to the invention are considered to be within the ability of those skilled in the art. Such changes and variations are intended by the inventors to be within the scope of the invention.

What is claimed is:

1. A personal care product comprising a top sheet, a surge layer and an absorbent core, wherein said surge layer is positioned between said top sheet and said absorbent core, said surge layer comprises a compression resistant creased first layer, a lower density second layer adjacent said first layer, said second layer having a density between 0.01 and 0.05 g/cc, and said second layer and said first layer being bonded together, wherein said first layer comprises a nonwoven web comprising polyolefin fibers.

2. The personal care product of claim 1, wherein said polyolefin is polypropylene.

3. The personal care product of claim 1, wherein said polyolefin fibers are polyethylene/polypropylene conjugate fibers.

4. The personal care product of claim 1, further comprising apertures in said first layer.

5. The personal care product of claim 1, wherein said first layer comprises a spunbond nonwoven web.

6. The personal care product of claim 1, wherein said second layer comprises conjugated fibers.

7. The personal care product claim 1, wherein said second layer is more wettable than said first layer.

8. The personal care product of claim 1, wherein said second layer is not creased.

9. The personal care product of claim 1, wherein said first layer comprises creases with a depth between 0.25 mm and 2 mm and a frequency between 5 and 100 creases per centimeter.

10. The personal care product of a claim 1, wherein said absorbent core comprises pulp.

11. The personal care product of claim 10, wherein said absorbent core further comprises a superabsorbent material.

12. The personal care product of claim 1, further comprising a backsheet.

13. The personal care product of claim 1, wherein said second layer fills the creased layer.

14. The personal care product of claim 1, wherein said personal care product is a feminine hygiene pad.

15. The personal care product of claim 1, wherein said personal care product is a diaper.

16. The personal care product of claim 1, wherein said personal care product is an adult incontinence product.

17. A personal care product comprising a top sheet, a surge layer and an absorbent core, wherein said surge layer is positioned between said top sheet and said absorbent core, said surge layer comprises a compression resistant creased first layer, a lower density second layer adjacent said first layer, a third layer adjacent said first layer on a side of the first layer away from said second layer, said second and third layers each independently have a density between 0.01 and 0.05 g/cc, and said second layer and said third layer are each independently bonded to said first layer.

18. The personal care product of claim 17, wherein said first and second layers are bonded together by a method selected from the group consisting of adhesive, mechanical, entanglement, thermal and ultrasonic means.

19. The personal care product of claim 17, wherein said second layer has been treated with a wettable surfactant.

20. The personal care product of claim 17, wherein said third layer is not creased.

21. The personal care product of claim 20, wherein said second layer is not creased.

22. The personal care product of claim 17, wherein said first layer comprises spunbond polyethylene/propropylene conjugate fibers and said second and third layers comprises uncreased spunbond polyethylene/polyproplyene fibers on either side thereof, said layers being bonded together by through-air bonding.

* * * * *